(12) United States Patent
Merkl et al.

(10) Patent No.: US 7,169,717 B2
(45) Date of Patent: Jan. 30, 2007

(54) METHOD OF PRODUCING A CALIBRATION WAFER

(75) Inventors: Christoph Merkl, Staig (DE); Markus Hauf, Ichenhausen (DE); Rolf Bremensdorfer, Bibertal (DE)

(73) Assignee: Mattson Thermal Products GmbH (DE)

( * ) Notice: Subject to any disclaimer, the term of this patent is extended or adjusted under 35 U.S.C. 154(b) by 0 days.

(21) Appl. No.: 10/536,788

(22) PCT Filed: Nov. 13, 2003

(86) PCT No.: PCT/EP03/12690

§ 371 (c)(1),
(2), (4) Date: May 26, 2005

(87) PCT Pub. No.: WO2004/049438

PCT Pub. Date: Jun. 10, 2004

(65) Prior Publication Data

US 2006/0040478 A1  Feb. 23, 2006

(30) Foreign Application Priority Data

Nov. 26, 2002 (DE) ................. 102 55 098

(51) Int. Cl.
*H01L 21/31* (2006.01)
*H01L 21/324* (2006.01)

(52) U.S. Cl. ............... 438/795; 374/1; 374/121; 374/126; 374/179; 257/E21.53

(58) Field of Classification Search ............... 438/795; 374/1, 121, 126, 179
See application file for complete search history.

(56) References Cited

U.S. PATENT DOCUMENTS

| 4,321,299 A * | 3/1982 | Frosch et al. ............... 442/379 |
| 4,890,245 A | 12/1989 | Yomoto et al. |
| 4,984,902 A * | 1/1991 | Crowley et al. ............... 374/1 |
| 5,154,512 A | 10/1992 | Schietinger et al. |
| 5,508,934 A | 4/1996 | Moslehi et al. |
| 5,624,590 A * | 4/1997 | Fiory ........................ 219/390 |
| 5,628,564 A * | 5/1997 | Nenyei et al. ............... 374/121 |
| 5,874,711 A * | 2/1999 | Champetier et al. ........ 219/497 |
| 5,994,676 A * | 11/1999 | Dutartre ..................... 219/497 |
| 6,171,641 B1 | 1/2001 | Okamoto et al. |
| 6,204,484 B1 | 3/2001 | Tay et al. |

FOREIGN PATENT DOCUMENTS

| DE | 38 03 336 | 8/1989 |
| EP | 0 618 430 | 10/1994 |
| EP | 0 910 115 | 4/1999 |
| WO | WO03/069668 | 8/2003 |

* cited by examiner

*Primary Examiner*—Asok Kumar Sarkar
(74) *Attorney, Agent, or Firm*—Dority & Manning, P A (57) ABSTRACT

A method of producing a calibration wafer having at least a predetermined emissivity, including providing a wafer of semiconductor material; subjecting the bulk material of the wafer to doping with foreign atoms and/or generating lattice defects to obtain the predetermined emissivity; and coating the wafer to obtain a further optical characteristic.

20 Claims, 4 Drawing Sheets

METHOD OF PRODUCING A CALIBRATION WAFER

This specification for the instant application should be granted the priority date of Nov. 26, 2002, the filing date of the corresponding German patent application 10255098.0 as well as the priority date of Nov 13, 2003 the filing date of International Application PCT/EP2003/012690.

BACKGROUND OF THE INVENTION

The present invention relates to a method of producing a calibration wafer having at least one predetermined optical characteristic, in particular a predetermined emissivity.

Computer chips, as well as other electronic components, are manufactured on round, disk-shaped semiconductor bodies, so-called wafers. During the manufacture, the wafers are subjected to various operations and processes. With some processes, it is necessary that the wafers follow a prescribed temperature curve. For example, coating processes of the wafers are frequently effected in that the wafers are subjected to a prescribed temperature curve during which they are disposed in a prescribed process atmosphere. It is also known to thermally treat wafers in a vacuum, and in particular as a post treatment process to preceding treatment steps. For example, a thermal treatment can heal damages in the crystalline lattice structure of the wafer that result as a consequence of an ion implantation.

In recent times, so-called RTP units (Rapid Thermal Processing) are used ever more frequently for the thermal treatment of the wafers, with such units also being designated as rapid heating units. Such units enable a rapid thermal treatment of the wafers under prescribed process conditions at temperatures of up to 1200° C. What is special about these units is not only the high treatment temperature, but also that heating rates of 200° C./s and more can be achieved. Due to these high heating rates, which ensure a high throughput of the RTP units, they have a significant economical advantage. Furthermore, high heating and cooling rates are in particular important for a successful treatment of very small structures, since a treatment at high temperatures is possible while at the same time the overall thermal budget of the thermal processing can be kept low.

However, the rapid heating-up rates also lead to a considerable loading of the wafers if they are not homogeneously treated over their entire surface. As a result, temperature differences can occur between different regions of the wafer, which can lead to a distortion of the wafer or the formation of crystalline structure imperfections or defects. A distortion or crystalline structure imperfection can destroy the structures or electrical contacts that are applied to the wafer, thus making the wafer unusable. Therefore, a homogeneous temperature distribution over the entire wafer is necessary. To achieve this, a permanent temperature measurement is effected during the thermal treatment for the control and regulation of the temperature curve or progress of the wafer. In this connection, a temperature measurement, in particular also at different points of the wafer, is effected in order to compensate for temperature inhomogeneities. A reliable temperature measurement is therefore a main feature of an RTP unit.

For the temperature measurement, pyrometry has proven to be particularly expedient, since it requires no contact with the wafer and furthermore does not adversely affect the actual heating of the wafer by sources of radiation. A temperature measurement in RTP units based on pyrometry, however, has basic problems due to an intensive radiation field within a processing chamber of the RTP unit. The radiation field, which is generally emitted from heating lamps, is customarily so great that it superimposes a temperature radiation that is emitted from the wafer and is to be measured by the pyrometer. This problem is intensified at low wafer temperatures since the wafers have a low emissivity at low temperatures. Due to the low emissivity of the wafers at low temperatures, however, the signal-to-background ratio is made even worse.

U.S. Pat. No. 5,154,512 discloses a method for measuring a wafer temperature in an RTP unit, according to which a periodic modulation is imparted to the heat radiation. This modulation enables a differentiation between the heat radiation emitted from the heat sources, and the heat radiation emitted from the wafer, since the modulation is not contained in the radiation of the wafer. In the known method, initially a measurement signal, which is composed of the wafer temperature radiation and a portion of the heat radiation reflected at the wafer surface, is measured with a first contact-free measuring instrument. A measuring signal of the heat radiation of the heat device is received by a second contact-free measuring instrument. In the known method it is presumed that the thermal mass of the wafer is so big that the wafer temperature cannot follow the imparted modulation of the heat radiation. Thus, it is possible to separate the non-modulated, weak wafer temperature radiation from the much greater, yet modulated, heat radiation metrologically. The wafer temperature can then be determined from the wafer temperature radiation.

With modern RTP units, the known method of the temperature measurement has been expanded and improved by a mathematical model. With this model, various radiation components of the unit, such as the occurrence of multiple reflections and others are taken into account. Therefore, the model contains a set of specific parameters with which geometrical and unit-specific factors are determined. The measurement signals measured in the measuring device are incorporated into this model, and the temperature of the wafer can be determined by means of the parameters of the model.

In this connection, in most cases a measurement of the parameters has turned out to be very difficult or, in practice, cannot be carried out. Therefore, it is necessary to have a starting calibration of the RTP unit at which values for the parameters of the model are determined by means of a calculation algorithm, with the parameters being as close to reality as possible. During the starting calibration, a plurality of calibration wafers having many different optical characteristics are measured at different temperatures, i.e. the temperature radiation emitted from the respective calibration wafers is measured.

At low temperatures, in particular temperatures below 600° C., however, the wafers have an increasing transparency for the heat radiation, which leads to a significant lowering of the emissivity and hence to a very low signal-to-background ratio. In practice, in particular metallic coated wafers are treated at low temperatures, with these wafers having much higher emissivity than do conventional calibration wafers. Therefore, in order to ensure a proper calibration even at low temperatures, special wafers having specific characteristics are necessary that have an emissivity that is similar to that of the wafers that are being treated at these low temperatures.

One possibility of making such a calibration wafer is to provide the calibration wafer with a metallic layer, and in particular similar to a wafer that is to be subsequently thermally treated. Due to the metallic layer, one achieves an adaptation of the emissivity of the calibration wafer to that of the wafer that is to be subsequently treated. However, this method has the drawback that the metallic layer can lead to an undesirable contamination of the unit. Furthermore, such metallic coatings are stable only in a limited temperature range, and therefore have only a limited use. If during the calibration process such wafers are heated to higher temperatures, the metal layer can peel off, which can lead to considerable contamination of the unit. Furthermore, the calibration wafer would be destroyed.

Therefore, for a good calibration it is important to make available calibration wafers which cover the ranges of temperature and emissivity that are relevant for the practice, i.e. that, at the respectively utilized temperature ranges, they have an emissivity that is similar to that of the wafers that are to be subsequently treated. At high temperatures, the wafers are optically opaque for the heat radiation, and therefore the emissivity at high temperatures can be altered merely over the reflectivity of the wafers if, for example, a suitable coating is selected. At low temperatures, where the wafer is essentially optically transparent for the heat radiation, an adjustment of the emissivity can be effected both via the reflectivity and the transmissivity.

It is therefore an object of the present invention to provide a calibration wafer that in a simple and economical manner has a predetermined optical characteristic, in particular a predetermined emissivity, that is adapted to the emissivity of the actually to be treated wafer, and with which there is no risk of metallic contamination of the unit.

SUMMARY OF THE INVENTION

Pursuant to the invention, this object is realized by a method of producing a calibration wafer having at least one predetermined optical characteristic, in particular a predetermined emissivity, with the method providing a wafer of a semiconductor material, as well as processing the bulk material of the wafer to obtain the predetermined optical characteristic by means of a doping with foreign atoms and/or a generation of lattice defects. The inventive method enables the production of special calibration wafers having predetermined optical characteristics. During the production, the desired optical characteristics can be obtained by manipulating the bulk material of the wafer. In this connection, in particular the transmission or transmissivity property of the wafer is altered at different characteristics, which again have a direct influence upon the emissivity of the wafer. By, for example, doping a wafer, it is possible to adjust the transmissivity property in a desired manner; in particular, it is possible to achieve a low transmissivity and a high emissivity of the wafer, even at low processing temperatures. By manipulating the bulk material, it is possible to dispense with a coating of the calibration wafer with a metallic layer, as a result of which the problems related thereto are eliminated. Furthermore, the calibration wafers can be produced economically, since a complicated and expensive coating can be eliminated. Furthermore, a manipulation of the bulk material results in the optical characteristics thereof, such as reflectivity, transmissivity and emissivity, remaining uniform over a long period of time. With coated wafers, the layer, in particular a metallic layer, can change due to oxidation, or a partial separation of the layer can occur due to thermal stresses between the metallic layer and the wafer disposed therebelow. The calibration wafers known up to now have the tendency that their optical characteristics are altered over time.

Pursuant to a preferred embodiment of the invention, the doping with foreign atoms and/or the generation of lattice defects over the entire bulk material of the wafer is effected essentially homogeneously in order to provide uniform optical characteristics. Pursuant to an alternative embodiment, the doping with foreign atoms and/or the generation of lattice defects is effected in a predetermined region, in particular in a layer of the wafer. In this connection, preferably a surface layer of the wafer is doped since such a layer is the easiest to dope.

The doping is advantageously effected with boron, phosphorous and/or arsenic as the foreign atoms. Furthermore, the establishment of the optical characteristics is preferably effected essentially exclusively via the doping and/or the establishment of the lattice defects in order to avoid further production steps, which would increase the cost for the production of the wafer.

To achieve desired optical characteristics, the wafer is preferably doped with a density of foreign atoms that lies between $10^{16}$ and $10^{19}$ foreign atoms per cubic centimeter.

Pursuant to a further embodiment of the invention, the establishment of the optical characteristics is effected at least partially via the selection of the thickness of the wafer, since wafers having different thicknesses, which have different transmissivities and emissivities, can be easily produced. The emissivity is preferably established to a value of 0.25 and 0.8. The reflectivity of the wafer is preferably established to a value between 0.2 and 0.8.

Pursuant to a further embodiment of the invention, the wafers are additionally coated to obtain the desired optical characteristic. By means of a coating, it is possible to establish in particular the reflectivity of the wafer to a desired value. In this connection, the wafer is preferably coated with cobalt.

During a calibration of an RTP unit, a plurality of calibration wafers, preferably calibration wafers having respectively different optical characteristics, are successively subjected in the unit to a simulated thermal treatment. In other words, the temperature of the wafers is altered along a prescribed temperature-time curve. During this simulated thermal treatment, the wafer radiation for all calibration wafers, at all temperatures, is determined with a first contact-free measuring device comprised of a first and second measuring instrument. Simultaneously, the actual wafer temperatures for all calibration wafers are measured with a second measuring device that is in contact with the calibration wafer. The last-mentioned measuring device delivers the actual wafer temperature, whereas the measurement signals delivered from the first contact-free measuring device are incorporated into a mathematical model. For the starting calibration, the parameter set of the model is provided with initially arbitrary values, from which, however, one knows from experience that they approximately represent the real parameter values. Based on these parameter values, the model calculates from all measurement signals a respective temperature value per calibration wafer and holding temperature that is respectively compared with the corresponding actual wafer temperature delivered from the second measuring device.

Proceeding from the differences of these value pairs, pursuant to a calculation algorithm new values are sought for the individual parameters until the temperature values calculated with this new parameter set and the measurement signals from the model adequately coincide with their corresponding actual temperature values for all calibration wafers and all holding temperatures. The values of this parameter set are then used for the parameters of the model during a normal processing operation of the unit with which one processes the wafers that are to be treated.

As previously mentioned, the use of metal-coated calibration wafers is possible only at low temperature ranges that are below approximately 600° C. At higher temperatures, in particular at temperatures of approximately 1000° C. to approximately 1100° C., the metal layer peels off, which leads to destruction of the calibration wafer and to contamination of a processing chamber of the RTP unit. Therefore, such wafers in high temperature ranges cannot be used for the calibration of an RTP unit. In addition, metal-coated wafers limit the atmospheres in which a calibration can be effected since the metals easily oxidize or reduce. With the inventive wafers, in contrast, the entire relevant temperature range of an RTP unit can be calibrated. Furthermore, the wafers are not as sensitive with regard to the processing atmosphere.

The same calibration wafers can be used not only for a calibration at low temperatures but also at high temperatures, so that a second set of calibration wafers, as would be necessary with metal-coated calibration wafers, is not necessary. In addition to the effect that the same set of calibration wafers can be used not only for low temperatures but also for high temperatures, thus requiring fewer calibration wafers, the time for the calibration process can be considerably reduced since fewer calibration wafers are introduced into the unit and must be measured.

The invention will be described in greater detail subsequently with the aid of preferred embodiments. The drawings show.

BRIEF DESCRIPTION OF THE DRAWINGS

DESCRIPTION OF SPECIFIC EMBODIMENTS

Figure 1:
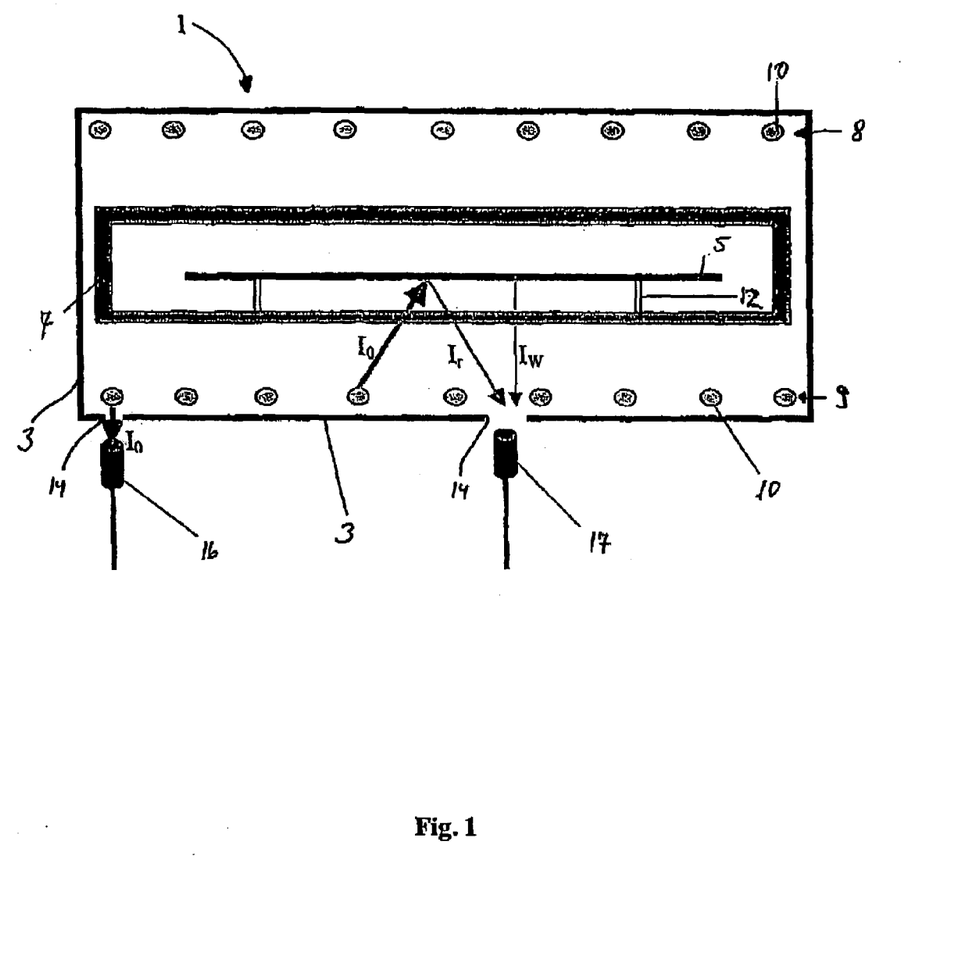
FIG. 1 a schematic view of an RTP unit.

FIG. 1 schematically shows the typical construction of an RTP unit 1, which is also designated as a rapid heating unit. The RTP unit has a housing 3, the inner walls of which are reflective. The housing 3 furthermore has a non-illustrated input/output opening for the loading and removal of semiconductor wafers 5. Provided within the housing 3 is a processing chamber 7 of a light-transparent material, such as quartz. The processing chamber 7 also has a non-illustrated input/output opening. As illustrated in FIG. 1, the processing chamber 7 is disposed centrally within the housing 3 in such a way that space exists above and below the processing chamber for upper and lower banks of lamps 8, 9 respectively. The banks of lamps 8, 9 are respectively formed of a plurality of lamps 10 that are disposed in a row. The lamps 10 are preferably rod-shaped tungsten-halogen lamps, whereby, however, other lamps can also be used. Although upper and lower banks of lamps 8, 9 are illustrated, it is of course also possible to use only a single bank of lamps, i.e. the upper or the lower bank.

The housing 3 and the processing chamber 7 have non-illustrated inlets and outlets for process gases in order to be able to produce a desired process atmosphere within the processing chamber 7.

Provided within the processing chamber 7 are support elements 12 for the wafers 5. The support elements 12 can, for example, be pin-shaped quartz elements on which a wafer can rest during a treatment, or a calibration wafer can rest during a calibration of the RTP unit. The support elements 12 are comprised of a light-transparent material in order to avoid shadow effects due to the support elements 12.

The housing 3 is furthermore provided with at least two openings 14 to form windows for a measuring device comprised of two non-contact measuring instruments 16, 17. In the illustrated embodiment, the measuring instruments 16, 17 are two pyrometers. However, other measuring instruments can also be used, such as a CCD array or other instrument for measuring radiation. In this connection, the pyrometer 16 is directed toward at least one of the lamps 10 of the lower bank of lamps 9 in order to detect the heat radiation $I_o$ emitted therefrom. The second pyrometer is directed toward one side of the wafer 5 and detects temperature radiation $I_W$ emitted from the wafer 5, and at the same time a portion $I_r$ of the heat radiation $I_o$ emitted from the lower banks of lamps 9 and reflected from the wafer 5. Furthermore, it is also possible to detect at the second pyrometer heat radiation from the upper bank of lamps 8 that passes through the wafer 5; however, this is not illustrated in FIG. 1.

The banks 10 of the upper and lower banks of lamps 8, 9 are controlled in a modulated manner, so that the heat radiation $I_o$ has a modulation. The heat radiation is comprised of a direct component $I_{ODC}$ and an alternating component $I_{OAC}$. In conformity therewith, the reflected portion $I_r$ of the heat radiation $I_o$ is composed of a direct component $I_{rDC}$ and an alternating component $I_{rAC}$. The modulation of the heat radiation is selected such that, due to the large mass of the wafer 5, and thus its thermal inertia, the modulation has no effect upon the radiation $I_W$ emitted from the wafer. The radiation $I_W$ emitted from the wafer therefore has no alternating component. On the whole, the pyrometer 9 detects a signal I that is composed of a direct component $I_{DC}$ and an alternating component $I_{AC}$.

By comparing the direct and alternating components $I_{ODC}$, $I_{OAC}$, $I_{DC}$ and $I_{AC}$ of the heat radiation $I_O$ detected by the pyrometer 8, and the radiation I detected by the pyrometer, the radiation $I_W$ emitted by the wafer can be determined. This radiation is incorporated into a mathematical model that, from the radiation components and a set of parameters that have certain values, calculates the temperature of the wafer 5. By means of the parameters, specific characteristics of the RTP unit are determined, such as geometrical factors that are a function of the shape of the housing 3 and the chamber 7, or other characteristics such as the reflection properties of the housing 3, but also the wave length or wave length ranges at which the pyrometers 16 and 17 operate.

In practice, most of these parameters are not determined by a measurement, but rather must be determined prior to the actual operation of the RTP unit with the aid of calibration measurements accompanied by a subsequent adaptation of the parameters via a mathematical algorithm.

This generally occurs with a set of four calibration wafers having optical characteristics that differ from one another, such as different reflectivities, emissitivites, etc. These four calibration wafers are placed into the unit 1, one after the other, and are brought to different temperatures for specific periods of time. In this connection, the respective temperature of the calibration wafer is measured with a measuring instrument of the contact type, such as a thermocouple element. This measuring instrument thus makes a reference temperature available for the calibration. At the same time, a measurement of the wafer radiation in the manner described above is effected via the pyrometers 16, 17.

The calibration wafers and the temperatures to which they are heated are selected such that the emissivity or reflectivity of the wafers at the temperatures are within a range in which wafers that are subsequently to be treated also lie. In other words, calibration wafers are used that have a reflectivity or emissivity that is similar to the wafers that are subsequently to be treated, and the calibration wafers are heated to temperatures to which the wafers that are subsequently to be treated are also heated. This is necessary in order to prescribe the mathematical model parameters that subsequently lead to correct temperature readings of the wafers that are to be treated. If the emissivity or reflectivity of the calibration wafer deviates too much from the wafers that are actually to be treated, no reliable indication can be taken with respect to the subsequently measured temperatures since the predictions of the mathematical model for these parameters were not checked.

Figure 2:
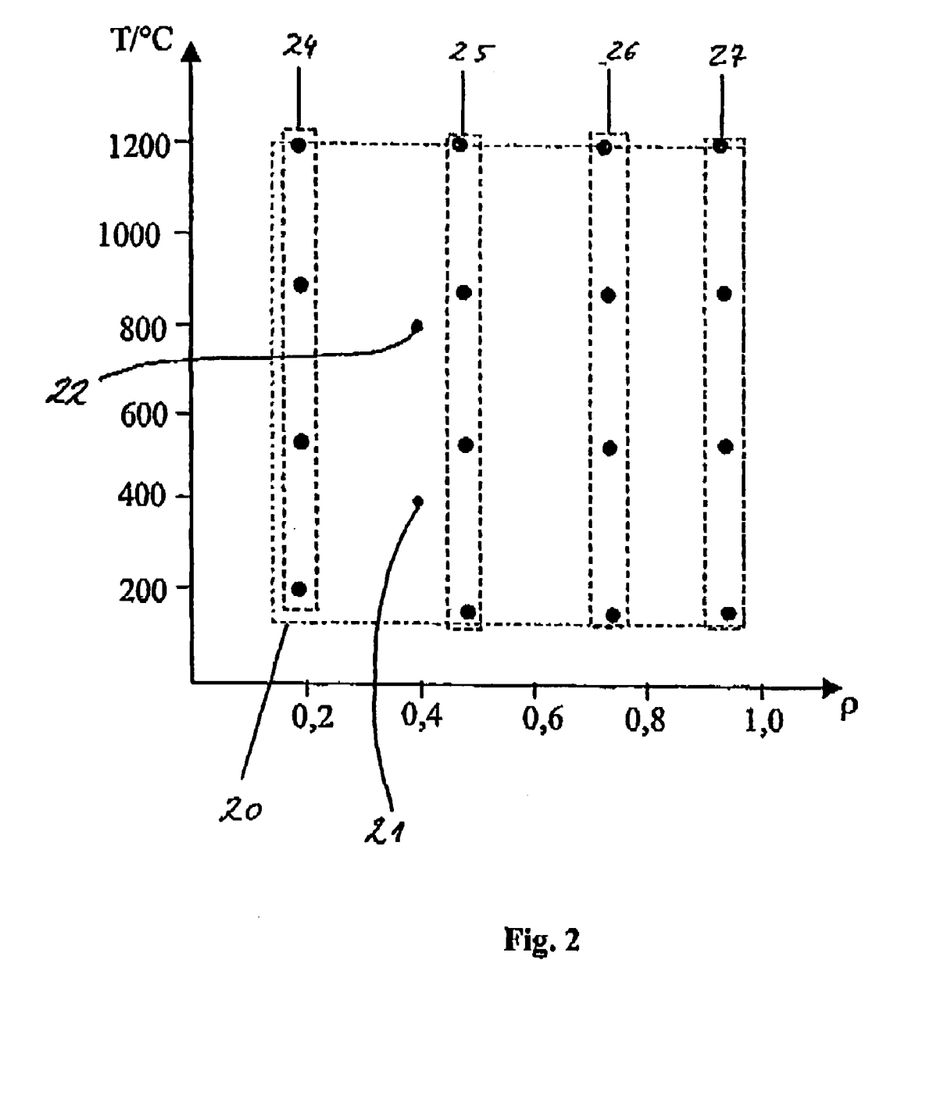
FIG. 2 a temperature-reflectivity graph in which, for four different wafers, the measurement points at respectively four different temperatures are plotted.

FIG. 2 shows a temperature-reflectivity graph. The dashed-line region 20 characterizes a region within the graph in which wafers to be treated can be found. In other words, the wafers can, for example, have a reflectivity of 0.4 at a temperature of 400° C., as illustrated by the point 21. Another wafer that is to be treated can have the same reflectivity, for example at a temperature of 800° C., as illustrated by the point 22.

To be able to calibrate this region 20 as broadly as possible, four calibration wafers having different reflectivities, as described above, are measured. For example, each of the wafers is heated to four different temperatures, and is held at this temperature for a specific period of time, whereby the actual temperature measurement is effected by means of a temperature measuring instrument of the contact type, such as a thermocouple element. While the temperature is maintained, the optical radiation that is respectively emitted by the wafers is measured, and the result is incorporated into the mathematical model. During the measurement of the four calibration wafers, the measuring points of which are respectively illustrated in the regions 24, 25, 26 and 27, there thus result 16 measurement points within the region 20. The possible change of the reflectivities of the calibration wafers as a function of the temperature was disregarded in the graph. Thus, each point represents a specific reflectivity at a specific temperature for a calibration wafer.

As previously mentioned, the pyrometer signals, in particular the pyrometer signals relating to the radiation emitted from the wafer, are now incorporated into the mathematical model, which calculates a temperature for each of the 16 points. At the beginning of the calibration, these 16 calculated temperatures are generally not the same as the corresponding value measured by the temperature-measuring instrument. Since for each calculated temperature, one forms a difference with the temperature measured by the temperature-measuring instrument, one obtains 16 temperature differences, which provide an indication of the quality of the established parameters of the model.

By means of a mathematical algorithm, the parameters of the model are now altered in order to reduce the 16 temperature differences. Subsequently, using the new parameter set, as well as the parameter signals, 16 new temperatures are calculated. The temperature differences to the actually measured temperatures are again determined in order on the basis of this difference to once again alter the parameters of the mathematical model. This process is repeated until a parameter set is established with which the temperatures calculated by the model with the aid of the pyrometer signals coincide with the temperatures measured by the temperature-measuring instrument. The RTP unit now has a calibrated parameter set that within the region 20 enables a reliable temperature measurement and control via the pyrometers 16, 17.

Pursuant to the present invention, the calibration wafers that are used in this connection are specially manufactured calibration wafers having specific optical characteristics, whereby the optical characteristics are obtained by manipulating the bulk material of the wafer. With the presently preferred embodiment of the invention, the manipulation of the optical characteristics, in particular the absorption of the bulk material, is effected by doping a conventional semiconductor wafer with foreign atoms. By means of the doping, the optical characteristics of the wafer, such as the reflectivity, the transmissivity, and the emissivity, can be adjusted to desired values.

Figure 3:
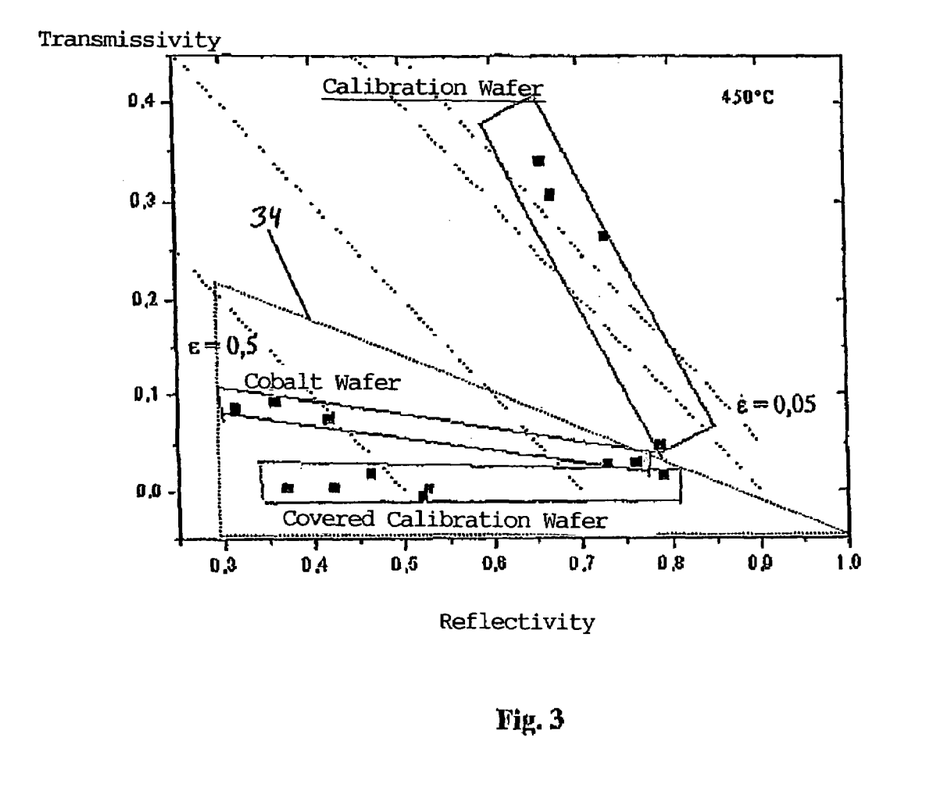
FIG. 3 a transmissivity-reflectivity graph for various types of wafers.

In FIG. 3, the relationship between reflectivity and transmissivity is illustrated in a graph for standardized calibration wafers, for wafers coated with cobalt, and for covered, standardized wafers. The dotted lines are lines of constant emissivity since the sum of emissivity, reflectivity and transmissivity is always 1. The graph represents the relationships for a fixed temperature of 450° C.

As can be seen in FIG. 3, the reflectivities of conventional calibration wafers in the illustrated situation lie between 0.65 and 0.8. The pertaining transmissivities lie in a range between 0.05 and 0.35.

The dotted triangle 34 designates the region in which are disposed wafers that are customarily to be treated. It is obvious that the conventional calibration wafer does not fall into this region, and is therefore not suitable for a calibration. In contrast, the wafers coated with cobalt, as well as covered wafers, fall into the region 34 and are thus suitable for calibration, although they also have the aforementioned drawbacks. Finally, pursuant to conventional methods customary calibration wafers are always brought into the region 34 by applying an appropriate coating. The covered wafers cover only an edge portion of the region 34.

With the inventive production of calibration wafers, the transmission characteristics, or the tranmissivity, can be adjusted to a desired value by suitable manipulation of the bulk material of a conventional semiconductor wafer. In particular, this is effected by means of a doping with foreign atoms, such as phosphorous, boron and arsenic, whereby phosphorous and boron are preferred.

Figure 4:
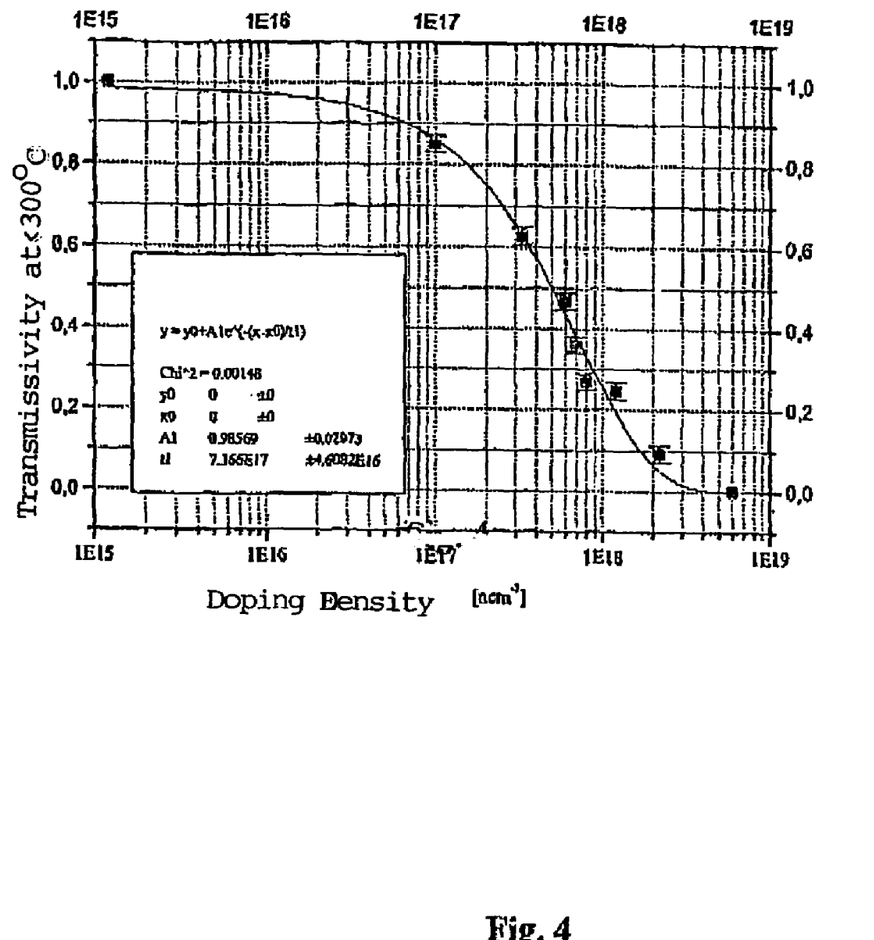
FIG. 4 a graph that shows the measured and simulated dependency of the transmissivity of a wafer upon the doping density at a selected measurement wave length.

In FIG. 4, the dependence of the transmissivity of a doped wafer for infrared radiation upon the density of doped foreign atoms is illustrated, and in particular for temperatures of less than 300° C. At a doping density of $10^{15}$ atoms per $cm^3$ the transmissivity is 1, i.e. the wafer is transparent for infrared radiation. If the doping density is increased, the transmissivity decreases continuously until, at a doping density of $10^{19}$ atoms per $cm^3$, it approaches zero, i.e. at this doping density the wafer is essentially opaque for infrared radiation.

It is thus possible to obtain every desired transmissivity for the wafer with foreign atoms by means of the doping density. Thus, a set of calibration wafers can be prepared that essentially entirely covers the region 34 desired in FIG. 3. Preferably, calibration wafers having a transmissivity of 0.3, an emissivity between 0.25 and 0.8, and a reflectivity between 0.2 and 0.8 are used.

The calibration wafers can be doped by any desired process. The doping can be carried out homogeneously over the bulk material. However, it can also be advantageous to vary a doping density within the wafers, or to only locally dope the wafers. It is in particular possible to dope only one or more layers of the wafer, whereby it is the most straightforward to provide such a doped layer at the surface of the wafer, or directly below the surface of the wafer.

As previously mentioned, the doping can be effected in any desired manner. Pursuant to one embodiment of the invention, the doping is effected by doping a silicon wafer of an appropriately enriched silicon melt. Doping profiles, which are produced by diffusion of the doping material into the wafer, are also suitable for the inventive production of the calibration wafers. If one desires to merely dope one layer within the wafer, ion implantation is particularly suitable. During the implantation of the doping material into the wafer, the crystalline structure of the latter is damaged, which can lead to a desired influencing of the optical characteristics. The crystalline structure can either remain in the destroyed state, or can be healed by a subsequent tempering, as a result of which doping atoms are also disposed on crystalline lattice locations, which results in a calibration wafer that is stable for a long period of time.

In place of doping, it is also possible to establish the optical characteristics of the wafer by altering the crystalline structure, in particular by generating lattice defects. In the following, the term lattice defects includes zero to three dimensional lattice defects. Zero dimensional defects are, for example, point type imperfections or point defects such as vacancies, EZG or interstitials, and chemical foreign atoms, which are disposed in the host or matrix lattice on intermediate or lattice positions or sites. Depending upon whether the defects are caused by host lattice atoms or foreign atoms, one speaks of intrinsic or extrinsic point defects. If the host lattice atoms that cause the vacancies migrate to the surface, there result Schottky defects; if these atoms migrate onto intermediate lattice sites, one speaks of Frenkel defects. An agglomeration of point-type imperfections can lead to higher dimensional lattice disorders, such as dislocation rings or dislocation lines (single dimensional defects), stacking imperfections (two dimensional defects), or precipitates of foreign atoms (three dimensional defects).

Further defects are, for example, crystal boundaries (two dimensional) or the already mentioned three dimensional precipitates (for example oxygen precipitates in silicon or metal precipitates), or the nucleation centers required for the formation of precipitates, as well as local amorphous regions that result, for example, during ion implantations, or voids. Crystalline like is intended to mean, for example, the transition region from crystalline to amorphous structure. As further defects, one could also mention the formation of F-centers (color centers), such as are present in ionic crystals, with which an electron resides in a halogen gap or interstice in the vicinity of adjacent cations.

Although the invention was described with the aid of preferred embodiments, the inventive concept is not limited thereto. For example, the optical characteristics of the calibration wafer can also be altered by varying the thickness of the wafer. For example, a set of calibration wafers can be formed of respectively uniformly homogeneously doped calibration wafers having different thicknesses. Furthermore, the previously mentioned features of the invention can be combined and modified in any compatible manner. For example, it is conceivable to coat the inventive calibration wafers, in addition to a manipulation of the material, for example with cobalt.

The specification incorporates by reference the disclosure of German priority document 102 55 098.0 filed Nov. 26, 2002 and PCT/EP2003/012690 filed Nov. 13, 2003.

The Present invention is, of course, in no way restricted to the specific disclosure of the specification and drawings, but also encompasses any modifications within the scope of the appended claims.

The invention claimed is:

1. A method of calibrating an RTP system, the method comprising:
   providing at least two calibration wafers, wherein the calibration wafers have differing predetermined reflectivities;
   successively subjecting each calibration wafer to a simulated thermal treatment comprising heat radiation;
   determining the temperature of each calibration wafer during thermal treatment using a contact-based measuring device that is in contact with the wafer;
   measuring radiation emitted from each calibration wafer during the simulated thermal treatment; and
   calculating a set of temperature measurement model parameters to correct temperature measurements based on measured radiation by comparing temperature measurements based on measured radiation to the actual temperature determined using the contact-based measuring device.

2. The method as set forth in claim 1, wherein the simulated thermal treatment comprises heating each calibration wafer to four different temperatures and holding the wafer at each temperature for a set period of time.

3. The method as set forth in claim 2, wherein the four different temperatures lie in a range from about 200° C. to about 1200° C.

4. The method as set forth in claim 1, wherein the calibration wafers comprise uncoated wafers doped to a transmissivity of about 0.0 to about 0.3 at the wavelength of the heat radiation.

5. The method as set forth in claim 4, wherein each of the four calibration wafers have different reflectivites ranging from about 0.2 to about 0.8; a transmissivity of about 0.3; and a emissivity between about 0.25 and 0.8 at the wavelength of the heat radiation.

6. The method as set forth in claim 1, wherein at least four calibration wafers are provided.

7. The method as set forth in claim 1, wherein providing a calibration wafer comprises:
   providing a wafer of semiconductor material;
   subjecting the bulk material of the wafer to at least one of doping with foreign atoms and generating lattice defects to adjust the predetermined emissivity; and
   coating the wafer to obtain a further optical characteristic.

8. A method according to claim 7, wherein said further optical characteristic is a predetermined reflectivity.

9. A method according to claim 7, wherein said emissivity is established to a value of between 0.25 and 0.8 at the wavelength of the heat radiation.

10. A method according to claim 7, wherein said at least one of doping with foreign atoms and generating lattice defects is effected essentially homogenously over the bulk material of the wafer.

11. A method according to claim 7, wherein said at least one of doping with foreign atoms and generating lattice defects is effected in a predetermined region.

12. A method according to claim 11, wherein said predetermined region is a layer of the wafer.

13. A method according to claim 11, wherein a surface layer of the wafer is doped.

14. A method according to claim 7, wherein doping is effected with at least one of boron, phosphorous and arsenic.

15. A method according to claim 7, wherein adjusting of the predetermined emissivity is effected essentially exclusively via said at least one of doping with foreign atoms and generating lattice defects.

16. A method according to claim 7, wherein the wafer is doped with a density of foreign atoms that is between $10^{16}$ and $10^{19}$ foreign atoms per cubic centimeter.

17. A method according to claim 7, wherein the predetermined emissivity is effected at least partially via a selection of the thickness of the wafer.

18. A method according to claim 7, wherein said further optical characteristic is a reflectivity of the wafer, and wherein the reflectivity is established to a value between 0.2 and 0.8 at the wavelength of the heat radiation.

19. A method according to claim 7, wherein the wafer is coated with a metallic layer to obtain the further optical characteristic.

20. A method according to claim 19, wherein the wafer is coated with cobalt.

* * * * *